US010702615B2

United States Patent
Patel et al.

(10) Patent No.: US 10,702,615 B2
(45) Date of Patent: Jul. 7, 2020

(54) NON-CONTACT ULTRASOUND GERMICIDE APPARATUS

(71) Applicant: The Ultran Group, Inc., State College, PA (US)

(72) Inventors: Kashyap Patel, Hoboken, NJ (US); Mahesh Bhardwaj, State College, PA (US); Michael Whetzel, Port Matilda, PA (US); Anuj Bhardwaj, Minneapolis, MN (US); Mikel Langron, State College, PA (US)

(73) Assignee: The Ultran Group, Inc., State College, PA (US)

( * ) Notice: Subject to any disclaimer, the term of this patent is extended or adjusted under 35 U.S.C. 154(b) by 335 days.

(21) Appl. No.: 15/786,885

(22) Filed: Oct. 18, 2017

(65) Prior Publication Data

US 2018/0126017 A1    May 10, 2018

Related U.S. Application Data

(60) Provisional application No. 62/409,942, filed on Oct. 19, 2016.

(51) Int. Cl.
  *A61L 9/00*   (2006.01)
  *A61L 2/025*  (2006.01)
  *A61L 2/26*   (2006.01)
  *A23L 3/30*   (2006.01)

(52) U.S. Cl.
  CPC ............. *A61L 2/025* (2013.01); *A23L 3/30* (2013.01); *A61L 2/26* (2013.01); *A23V 2002/00* (2013.01); *A61L 2202/11* (2013.01); *A61L 2202/122* (2013.01); *A61L 2202/24* (2013.01)

(58) Field of Classification Search
  CPC .... A61L 2/00; A61L 2/025; A61L 2/14; A61L 12/026
  USPC ................... 422/1, 20, 127–128, 305–306
  See application file for complete search history.

(56) References Cited

U.S. PATENT DOCUMENTS

| 6,311,573 | B1 | 11/2001 | Bhardwaj |
| 7,125,468 | B2 | 10/2006 | Bhardwaj |
| 7,382,082 | B2 | 6/2008 | Bhardwaj |
| 7,791,253 | B2 | 9/2010 | Bhardwaj |
| 2014/0154795 | A1* | 6/2014 | Lipkens .............. B06B 1/0644 435/297.2 |

OTHER PUBLICATIONS

Hoover et al., "Destruction of Bacterial Spores by Phenomenally High Efficiency Non-Contact Ultrasound Transducers", Mat Res Innovat, (2002), pp. 291-295, 6.

\* cited by examiner

*Primary Examiner* — Monzer R Chorbaji
(74) *Attorney, Agent, or Firm* — The Webb Law Firm

(57) ABSTRACT

An apparatus for sterilization of objects or materials comprises an enclosure for containing a gaseous atmosphere; an acoustically transparent platform located within the enclosure for supporting the objects or materials to be sterilized; one or more non-contact ultrasound transducers positioned within the enclosure and spaced from the platform; and an electric power amplifier for exciting the one or more transducers.

4 Claims, 2 Drawing Sheets

NON-CONTACT ULTRASOUND GERMICIDE APPARATUS

CROSS REFERENCE TO RELATED APPLICATIONS

This application claims the benefit of U.S. Provisional Patent Application No. 62/409,942, filed Oct. 19, 2016, the disclosure of which is hereby incorporated by reference in its entirety.

BACKGROUND OF THE INVENTION

Field of the Invention

This patent application is directed to an apparatus for sterilization of food, materials, medical and surgical equipment, and the like using ultrasound transmitted through a gas atmosphere to the item to be sterilized, that is, via non-contact ultrasound (NCU).

Description of Related Art

Ultrasound transducers are the devices that transform mechanical energy into electrical energy and visa versa. Our invention makes use of NCU transducers. NCU transducers are based on the following two major inventions: 1) Piezoelectric transducers featuring substantially perfect impedance matching layers that deliver high intensity ultrasound waves in the gaseous media; and 2) Gas Matrix Piezoelectric (GMP) composites, the piezoelectric coupling factors of which are extremely high, thus increasing the efficiency of any ultrasonic device based on GMP.

NCU transducers are described in the disclosures of U.S. Pat. Nos. 6,311,573, 7,125,468, 7,382,082, and 7,791,253 which are incorporated herein by reference.

The power generated by such transducers is sufficient to destroy bacterial spores, as is evident in the following paper: Destruction of Bacterial Spores by Phenomenally High Efficiency Non-Contact Ultrasound Transducers, Kelli Hoover, Mahesh Bhardwaj, Nancy Ostiguy, Owen Thompson, Mat Res Innovat, (2002), 6.291-295.

SUMMARY OF THE INVENTION

It is an advantage, according to this invention, to provide an apparatus for safely and efficiently sterilizing objects and materials.

Briefly, according to this invention, there is provided an apparatus for sterilization of objects or materials comprising an enclosure for containing a gaseous atmosphere; an acoustically transparent platform located within the enclosure for supporting the objects or materials to be sterilized; one or more non-contact ultrasound transducers positioned within the enclosure and spaced from the platform; and an electric power amplifier for exciting the one or more transducers.

According to an alternate embodiment, one or more ultrasound reflectors are positioned within the enclosure and spaced across the platform from the one or more non-contact ultrasound transducers.

According to yet another embodiment, the enclosure is sealable to hold a pressurized gas and is provided with ports for introducing pressurized gas.

Preferably, the non-contact transduces are NCU transducers having a power output of at least 4 Watts per square centimeter of the surface area of the transducers.

DESCRIPTION OF THE DRAWINGS

Further features and objects and advantages will become apparent from the following detailed description made with reference to the drawings in which.

DESCRIPTION OF THE INVENTION

It is well-known that foods, particularly the processed foods, can occasionally get contaminated by unwanted bacteria or other germs during and or after the food processing. If unknown and ingested, this could and has caused unwanted diseases, even death in some cases. Therefore, it is highly desirable that processed foods or those that are susceptible to degradation be treated by some mechanism that would destroy the unwanted germs in them. Similarly, medical and surgical tools and implements in hospitals and clinics are contaminated after a patient has been treated and that such implements, must be sterilized and disinfected for repeated use. To this effect, common practices are: heat; steam-assisted heat; x-ray; electron beam; ultraviolet light; and others. These methods are effective, but not without limitations.

Whereas ultrasound is well-known for materials testing and for non-invasive medical diagnostics, it is also used in power applications, such as for welding and sealing materials, particle size reduction, cell degradation, and even chemical composition transformation. However, in order to accomplish such objectives either the ultrasonic transducer (a device that generates and receives ultrasound) is in direct contact with the material to be treated or it is immersed in some liquid medium, generally aqueous.

If one wished to disinfect foods or medical-surgical implements by using high power ultrasound with direct contact of the transducer or by submerging them in liquids for desired treatment, it is highly likely that things to be treated would be contaminated. In order to overcome such limitations, in this invention we utilize transducers that are characterized by extremely high transduction of ultrasound in air and in other gases generating high power ultrasound in the gaseous medium.

Figure 1:
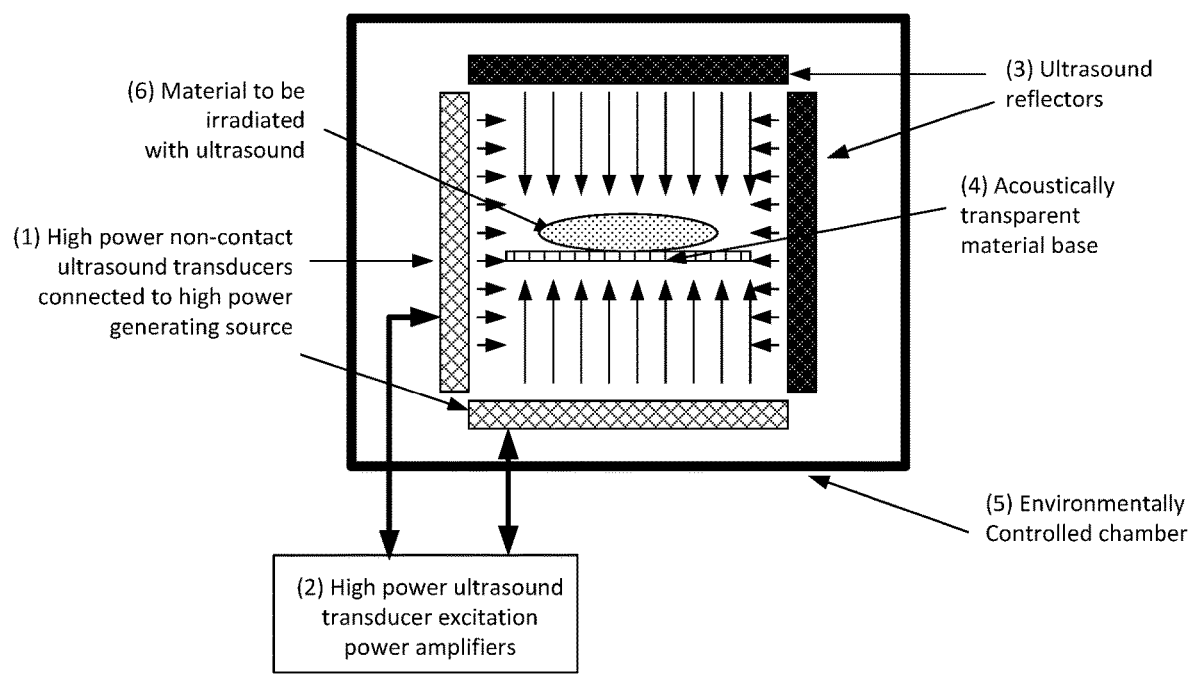
FIG. 1 is a schematic diagram of key elements of a first embodiment of this invention.

Referring now to FIG. 1, a first embodiment of this invention is now described. The utilization of two transducers and two ultrasonic reflectors and other key elements of this embodiment are illustrated in FIG. 1. Gas impervious walls define the volume of the enclosure. The enclosure may be provided with a sealable door or lid for inserting and removing items to be sterilized. The enclosure may have ports for introducing pressurized gas and venting the enclosure. High power non-contact ultrasound transducers 1 such as described in, but not limited to, U.S. Pat. Nos. 6,311,573, 7,125,468, 7,382,082, and 7,791,253 are specifically arranged and excited with one or more high power ultrasound power amplifiers 2. Ultrasound reflectors 3 are installed opposite of NCU transducers so that reflected ultrasound energy is effectively utilized to disinfect foods or other objects to be irradiated. Preferably, ultrasound reflectors 3 are very high acoustic impedance materials, such as steels or dense ceramics, such as aluminum oxide.

In the center of this apparatus is an acoustically transparent material platform 4, such as cotton fabric, cheese cloth, plastic fiber mesh, or like material. The material 6 to be treated is placed on the acoustically transparent material platform 4. The entire assembly is encased in a chamber 5 which can be environmentally controlled and pressurized to further increase the intensity of NCU transducers 1, thus making the process of disinfection even more efficient. NCU transducers are commercially available from the assignee of this application, The Ultran Group, Inc. (ultrangroup.com). High power amplifiers for driving the NCU transducers output sine wave electrical signals in the frequency range of 10 kHz to 12 MHz and maximum nominal output at 100 watts.

Figure 2:
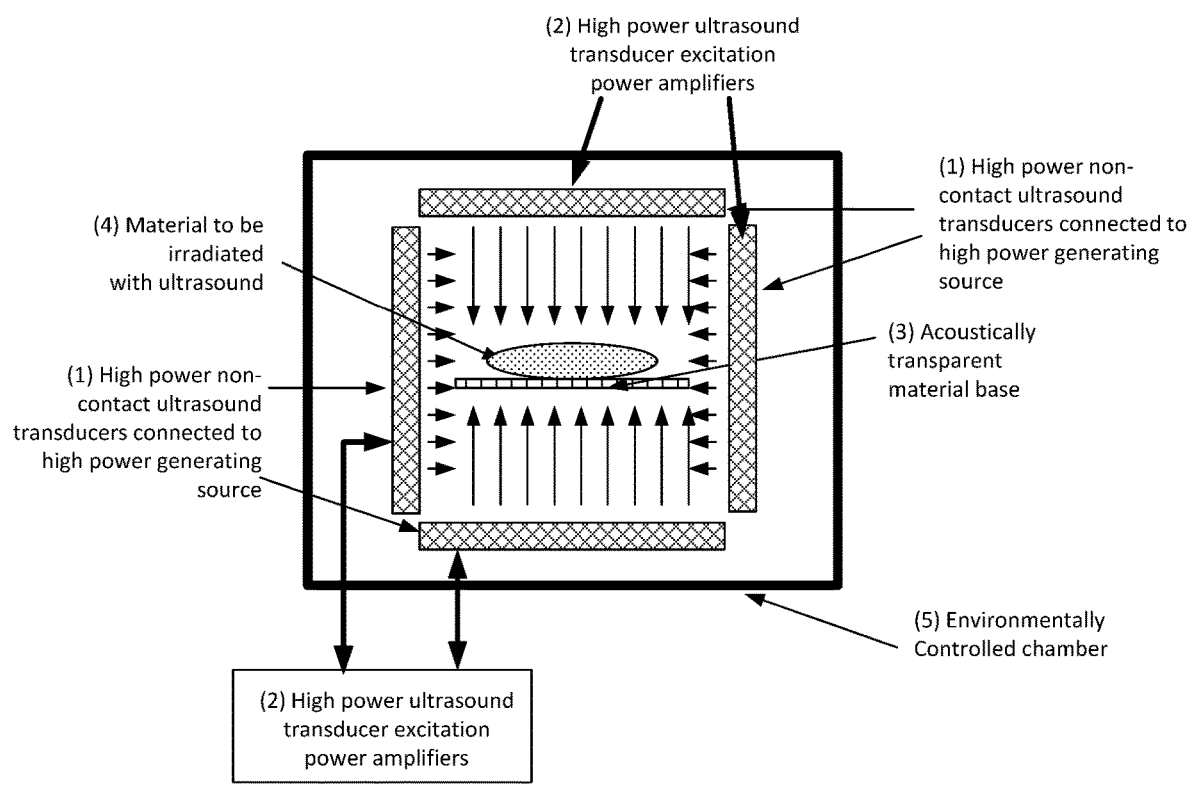
FIG. 2 is a schematic diagram of key elements of a second embodiment of this invention.

Referring now to FIG. 2, a second embodiment is described. The utilization of four NCU transducers and other key elements of this setup are illustrated in FIG. 2. High power NCU transducers 1 such as described in, but not limited to, U.S. Pat. Nos. 6,311,573, 7,125,468, 7,382,082, and 7,791,253 are specifically arranged and excited with one or more high power ultrasound power amplifiers 2.

In the center of this apparatus is an acoustically transparent material platform 4, such as cotton fabric, cheese cloth, plastic fiber mesh, or like material. The material 6 to be treated is placed on the acoustically transparent material platform 4. The entire assembly is encased in a chamber 5 which can be environmentally controlled and pressurized to further increase the intensity of NCU transducers 1, thus making the process of disinfection even more efficient.

NCU transducers have been successfully developed in broad frequency range, ~30 kHz to >5.0 MHz, and in dimensions from <1 mm to >250 mm. For bacterial spores destruction, we have successfully used these transducers of 30 kHz, 50 kHz, 100 kHz, 140 kHz, and 200 kHz frequencies with active area dimensions from 50 mm to 250 mm. We have also observed high ultrasound power from NCU transducers in ambient air at frequencies, such as 350 kHz, 500 kHz, 1.0 MHz, and higher. When NCU transducers are operated in high gas pressures, order of magnitude improvement in efficiency has been observed, thus making them highly suitable for the objectives of this invention.

Having thus defined our invention with the detail and particularity required by the Patent Laws, what is desired protected by Letters Patent is set forth in the following claims.

The invention claimed is:

1. An apparatus for sterilization of objects or materials comprising:
    an enclosure for containing a gaseous atmosphere;
    an acoustically transparent platform located within the enclosure for supporting the objects or materials to be sterilized;
    a plurality of non-contact ultrasound transducers positioned within the enclosure and spaced from the platform, the plurality of non-contact ultrasound transducers at least partially surround the platform; and
    an electric power amplifier for exciting the one or more transducers.

2. The apparatus according to claim 1, in which the ultrasound transducers are NCU transducers.

3. The apparatus according to claim 1, in which the ultrasound transducers transmit at least 4 watts per square centimeter of transducer surface into the gaseous atmosphere within the enclosure.

4. The apparatus according to claim 1, having one or more ultrasound reflectors positioned within the enclosure and spaced across the platform from the one or more non-contact ultrasound transducers.

\* \* \* \* \*